(12) United States Patent
Watterson

(10) Patent No.: US 10,293,175 B2
(45) Date of Patent: May 21, 2019

(54) DEVICE INCLUDING MOVING MAGNET CONFIGURATIONS

(76) Inventor: Peter Andrew Watterson, Ultimo (AU)

( * ) Notice: Subject to any disclaimer, the term of this patent is extended or adjusted under 35 U.S.C. 154(b) by 516 days.

(21) Appl. No.: 14/006,054

(22) PCT Filed: Mar. 16, 2012

(86) PCT No.: PCT/AU2012/000276
§ 371 (c)(1),
(2), (4) Date: Dec. 30, 2013

(87) PCT Pub. No.: WO2012/126044
PCT Pub. Date: Sep. 27, 2012

(65) Prior Publication Data
US 2014/0163305 A1   Jun. 12, 2014

(30) Foreign Application Priority Data
Mar. 18, 2011 (AU) .................. 2011900985

(51) Int. Cl.
*A61N 2/00*   (2006.01)
*A61N 2/06*   (2006.01)
*A61N 2/12*   (2006.01)

(52) U.S. Cl.
CPC .............. *A61N 2/12* (2013.01); *A61N 2/06* (2013.01); *A61N 2/006* (2013.01); *A61N 2/008* (2013.01)

(58) Field of Classification Search
CPC ............................................. A61N 2/00–2/12
USPC ....................................................... 600/9–15
See application file for complete search history.

(56) References Cited

U.S. PATENT DOCUMENTS

| | | | |
|---|---|---|---|
| 5,632,720 A * | 5/1997 | Kleitz ................. | A61N 2/00 600/9 |
| 6,123,657 A | 9/2000 | Ishikawa | |
| 2006/0253051 A1* | 11/2006 | Milne .................. | A61H 7/001 601/15 |
| 2008/0287730 A1* | 11/2008 | Spiegel ................ | A61N 2/004 600/9 |
| 2009/0082690 A1* | 3/2009 | Phillips ................ | G06Q 50/22 600/544 |
| 2010/0081858 A1* | 4/2010 | Sotiriou .............. | A61N 2/12 600/13 |
| 2011/0112427 A1* | 5/2011 | Phillips ............... | A61B 5/048 600/544 |
| 2011/0118536 A1 | 5/2011 | Phillips et al. | |
| 2013/0207759 A1* | 8/2013 | Nakamichi ........... | H01F 7/02 335/302 |

FOREIGN PATENT DOCUMENTS

| | | | |
|---|---|---|---|
| CA | 2 660 083 | 2/2008 | |
| DE | 3417773 A1 * | 2/1985 | ............... A61N 2/12 |
| DE | 29823196 U1 | 6/1999 | |
| JP | 2004-267353 A | 9/2004 | |

(Continued)

OTHER PUBLICATIONS

USPTO Human Translation of DE3417773, Mar. 1, 2018.*

*Primary Examiner* — Catherine B Kuhlman

(57) ABSTRACT

This invention relates to devices and methods for the activation of nerve cells and muscles by magnetic induction, and in particular to devices including moving magnets. The devices disclosed may also have other therapeutic, medical and industrial applications.

9 Claims, 8 Drawing Sheets

(56) References Cited

FOREIGN PATENT DOCUMENTS

| WO | 1996/015829 A2 | 5/1996 |
|---|---|---|
| WO | 1999/000158 A1 | 1/1999 |
| WO | 1999/039769 A1 | 8/1999 |
| WO | 00/45692 A2 | 8/2000 |
| WO | 2004/093992 A1 | 11/2004 |
| WO | 2005/123188 A1 | 12/2005 |

* cited by examiner

DEVICE INCLUDING MOVING MAGNET CONFIGURATIONS

CROSS-REFERENCE TO RELATED APPLICATIONS

This application claims priority to International Application No. PCT/AU2012/000276 filed on Mar. 16, 2012, which claims priority to Australian Patent Application No. 2011900985, filed Mar. 18, 2011, both of which are incorporated by reference in their entirety.

FIELD OF THE INVENTION

This invention relates to devices and methods for the activation of nerve cells and muscles by magnetic induction, and in particular to devices including moving magnets. The devices disclosed may also have other therapeutic, medical and industrial applications.

BACKGROUND

Many medical treatments, some in clinical use, others being trialled, involve activation of nerves. The most commonly used technique employs electric probes which inject current in the vicinity of the nerve. Several companies sell fully-implanted neurostimulators based on this technique to treat a variety of disorders including: pain from back, leg or peripheral nerves (neuropathy), by masking the pain with a tingling sensation; incontinence; movement disorders including Parkinson's disease; and obsessive-compulsive disorder. While such electrical devices use very little power to generate their voltage pulses, they are invasive and they require surgery every few years for battery replacement. External Transcutaneous Electrical Nerve Stimulation (TENS) can also activate surface nerves to mask pain, but these devices must pass current through the skin's resistance. TENS is also used to produce muscle contraction for various purposes, including prevention of muscle atrophy in immobilised patients, testing of muscle properties and strength training for sport, but the pain felt from activation of nociceptive receptors due to, the current through the skin limits such applications (see e.g. Gondin J., Cozzone P. J. & Bendaham D. "Is high-frequency neuromuscular electrical stimulation a suitable tool for muscle performance improvement in both healthy humans and athletes?" *Eur. J. Appl. Physiol.* 2011, 111:2473-2487).

The cost, inconvenience and infection risk of the implanted electrical devices have motivated development of external non-invasive devices based on magnetic induction. A changing magnetic flux density penetrating the body from the outside generates an electric field inside the body by Faraday's Law. Several companies sell systems that create a time-varying magnetic field by discharging a capacitor bank to produce a pulse of high current in a coil placed against the skin. These systems have major deficiencies. They are large (e.g. trolley-mounted) and expensive devices, and so their use requires visits to a clinic. The high currents entail high Ohmic heating in the coils. If high pulse repetition frequency is used, pumped liquid cooling is needed through the coils, adding to complexity. Some commercial systems can sustain up to 100 Hz with liquid cooling, but only at a fraction (e.g. 30%) of full amplitude. This is a lower frequency than the maximum human nerve firing rates, which are up to typically 300 Hz. The postsynaptic effect of a nerve pulse train is proportional to the pulse frequency, and so even the best pulsed coil systems do not achieve the high frequencies and amplitudes that could be beneficial in some medical treatments. Alternating current transcutaneous stimulation of frequency 2,500 Hz was once preferred in the training of Russian athletes, though one study found 1,000 Hz optimal if applied over the nerve trunk (Ward R. "Electrical Stimulation Using Kilohertz-Frequency Alternating Current", *Physical Therapy* 2009, 89:181-190).

The potential for moving permanent magnets to provide the time-varying magnetic field for inductive neurostimulation presents a possible means to obviate the drawbacks of the pulsed current systems. A small permanent magnet device would be cheap enough for a patient to take home and keep, implying no travel to a clinic, and they could use the device indefinitely, maintaining its benefits.

U.S. Pat. No. 6,648,812 to Ardizzone describes a device which rotates a spherical magnet about two axes, but the patent does not claim nerve or muscle electrical activation. A device called "Biaxial Powermag" sold by Nikken Inc. with reference to that patent rotates at up to 1,600 revolutions per minute (rpm) ("Applied science that is revolutionary. Magnetic Biaxial Rotation", Nikken Inc., 2007).

Theories modelling the activation of nerves generally focus on the "activating function", the gradient along the axon of the electric field component parallel to the axon (see for example Holsheimer J. "Principles of neurostimulation", Chap. 3 of *Electrical Stimulation and the Relief of Pain, Pain Research and Clinical Management Vol.* 15, Ed. Simpson B. A., Elsevier Science, 2003). The axon is surrounded by a membrane comprising segments of insulating myelin sheath, interrupted by the Nodes of Ranvier where ion channels are concentrated. The activating function is the key driving term in the "cable equation" for the rate of change of the transmembrane electric potential (see for example Nagarajan S. S. & Durand M. D. "A generalized Cable Equation for Magnetic Stimulation of Axons", *IEEE Trans. on Biomed. Engineering* 1996, Vol. 43, pp. 304-312). In simplified terms, the electric field gradient along the axon causes a converging ion flow inside the axon, because the ions inside the axon are largely trapped by its membrane while it is insulating, i.e. up until the nerve is activated and the ion channels open. The charge build-up in the tissue outside the nerve is much less because circulating currents can form there (though with some restriction from the boundary condition of zero perpendicular current across the skin). The electric potential build-up in the nerve is the product of its mean rate of change multiplied by its duration. Thus the product of the electric field gradient times its duration should be considered. Moving magnet configurations are sought which will create a sufficiently high product of electric field gradient times duration along a nerve fibre to stimulate the nerve action potential.

It is possible that a high electric field gradient may also produce activation of a muscle cell membrane directly, i.e. without first activating a nerve. The skeletal muscle fibre membrane (or sarcolemma) is electrically active, carrying action potentials along the long thin muscle fibre (see e.g. Keynes R. D. & Aidley D. J. *Nerve and Muscle* Third Ed., Cambridge University Press, 2001), and the membrane could be stimulated by electrical field gradients along the muscle fibre in a similar way as for a nerve fibre.

Some studies have found that a curved nerve can be stimulated through the curvature introducing a gradient of the electric field component along the nerve with respect to differentiation along the curved nerve path (see e.g. Rotem A. & Moses E. "Magnetic Stimulation of Curved Nerves", *IEEE Trans. on Biomedical Engineering* 2006, Vol. 53(3), pp. 414-420). At such a bend in a nerve, a high electric field amplitude is needed rather than a high electric field spatial (i.e. relative to fixed spatial coordinates) gradient (see e.g. Maccabee P. J., Amassian V. E., Eberle L. P. & Cracco R. Q. "Magnetic coil stimulation of straight and bent amphibian and mammalian peripheral nerve in vitro: locus of excitation", *J. Physiology* 1993, Vol. 460, pp. 201-219).

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

SUMMARY OF THE INVENTION

The present invention seeks to provide configurations of magnets, typically permanent magnets, which when rotated at high speed create high gradient of the electric field component along a nerve fibre for sufficient time to activate the nerve. The magnetic configurations disclosed herein generally employ several magnets positioned and aligned so that the electrical field gradients generated by the magnets all combine at a certain position (or positions) to create a sufficiently large sum to achieve nerve activation there. The electrical field gradient at the point oscillates sinusoidally in time and nerve activation occurs after a time interval of negative electric field gradient, sufficient to trigger the nerve action potential.

While the focus of the present invention is to establish configurations with a high gradient of electric field, capable of stimulating straight nerves, the configurations also feature high amplitudes of electric field which may benefit in stimulating nerves at positions where they are curved.

The present invention also seeks to provide a method of producing the rotation of the magnet configurations by interaction of the magnets of the configuration with electric currents in coils displaced around the stationary housing surrounding the magnet configuration. This is much more compact and more mechanically stable than having a motor separate to the magnet configuration, for example with both the motor and the magnet configuration each having their own pair of bearings and with their shafts joined by a coupling.

In one broad form, the present invention provides a device including a rotatable configuration of one or more magnets wherein rotation of the configuration of one or more magnets produces an electric field in a volume around or adjacent to the device.

In one form, the configuration of one or more magnets includes a first magnet positioned adjacent to a second magnet.

In a further form, the first magnet and the second magnet are cylindrical and diametrically magnetised.

In another form, the magnetisation direction of the first magnet is aligned anti parallel to the magnetisation direction of the second magnet.

In one form, the configuration of one or more magnets includes a quadrupole arrangement of magnets.

In another form, the configuration of one or more magnets includes: a first magnet and a second magnet wherein the first magnet and the second magnet are cylindrical and diametrically magnetised, the magnetisation directions of the first magnet and the second magnet being aligned anti-parallel; and, a magnetic disc formed of two substantially semicircular halves, the halves being axially magnetised in opposite directions, wherein the disc is positioned between the first magnet and the second magnet.

In one form, the configuration of one or more magnets includes a first magnet in the shape of a substantially semicircular prism, and a second magnet in the shape of a substantially semicircular prism, the first and second magnets being axially magnetised in opposite directions.

In another form, the configuration of one or more magnets includes a first magnet in the shape of a substantially semicircular prism, and a second magnet in the shape of a substantially semicircular prism, the first and second magnets being diametrically magnetised in opposite directions.

In one form, the configuration of one or more magnets comprises a single cylindrical magnet, diametrically magnetised.

In one form, the configuration of one or more magnets includes a first set of four alternating magnetic poles positioned around the axis of rotation of the configuration.

In a further form, the device includes a second set of four alternating magnetic poles positioned around the axis of rotation of the configuration, the second set being positioned adjacent the first set such that the polarity of the magnetic poles of the first set are opposite to the adjacent magnetic poles of the second set.

In another form, the configuration of one or more magnets is positioned on a rotating member within a housing, the rotating member being rotatable with respect to the housing.

In another form, the configuration of one or more magnets is encased within a casing.

In one form, the device generates an electric field whose component along a line has a high gradient along that line.

In another form, the device generates an electric field whose component along a line reverses in direction along that line, resulting in an electric field component which for half the electric field oscillation period converges along the line towards the point at which the electric field component vanishes and which for the other half of the oscillation period diverges from that point.

In one form, the device generates an electric field capable of activating a nerve.

In another form, the device generates an electric field capable of activating a muscle fibre directly.

In one form, the electric field is applied to provide a therapeutic effect.

In one form, the device includes at least two coils positioned around the configuration of one or more magnets, each of the at least two coils being arranged to receive a current and to thereby produce a related magnetic field, the magnetic field of the at least two coils cooperating to interact with the magnetic field of the magnet configuration to rotate the configuration of one or more magnets.

In another form, the device includes three coils around the configuration of one or more magnets with the coils arranged to receive a three-phase alternating current.

In one form, the device includes three coils each spanning approximately 120 degrees with respect to the direction of rotation of the rotatable configuration, two of the coils positioned at one end of the rotatable configuration with respect to the axis of rotation of the device and the third coil positioned at the other end with respect to the axis of rotation of the device, wherein the three coils are arranged substantially on a first side of the rotatable configuration with respect to the axis of rotation.

In another form, the configuration of one or more magnets includes at least one permanent magnet.

In another form, the configuration of one or more magnets includes at least one electromagnet.

In a further form, the device is sized to be handheld.

In a further form, the device is a nerve stimulation/activation device.

In another form, the device is a muscle stimulation/activation device.

In a further form the configuration of one or more magnets rotates at a speed exceeding 10,000 revolutions/minute.

In another form, supporting bearings are located internal to the casing and the outer race of the bearings is fixed to rotate with the casing.

In one form, the present invention provides a method of producing a therapeutic effect on a subject, the method including locating the device according to any one of the above forms in a position wherein the electric field produced by the rotation of the configuration of one or more magnets of the device permeates the subject.

In one form, the therapeutic effect is used to provide a treatment for pain, to generate localised hyperthermia, to aid in wound healing, to provide nerve regeneration, to provide muscle conditioning, to increase blood flow, to heat tissue, and/or to provide sexual stimulation.

In another form, the therapeutic effect involves the activation of a nerve of the subject.

In a further form, the therapeutic effect involves the activation of a muscle of the subject either directly, or indirectly through activation of a nerve.

In one form, the present invention provides a method of obtaining diagnostic information about the nerves or muscles of a subject, the method including locating the device according to any one of the above forms in a position wherein the electric field produced by the rotation of the configuration of one or more magnets of the device activates either the nerves or the muscles of the subject.

In one form, the present invention provides a method for activating a nerve of a subject, the method including positioning a device according to any one of the above forms in the vicinity of the nerve, and rotating the rotatable configuration of one or more magnets to generate an electric field of sufficient magnitude and/or gradient to activate the nerve.

In a further form, the present invention provides a method for stopping the passage of a nerve action potential along a nerve of a subject, the method including positioning a device according to any one of the above forms in the vicinity of the nerve and rotating the configuration of one or more magnets to generate an electric field which is of sufficient magnitude and/or gradient to stop the passage of the nerve action potential.

In one form, the configuration of one or more magnets is rotated at a first speed, the first speed being below an activation speed which would activate the nerve but above a minimum speed required to generate an electric field which is of sufficient magnitude and/or gradient to stop the passage of the nerve action potential.

In one form, the present invention provides a method of transmitting electrical power across the skin the method including positioning a device according to any one of the above forms in the vicinity of the skin under which coils appropriately shaped for the particular magnetic configuration of the device have been placed to receive the electric fields generated by the device.

In a further broad form, the present invention provides a method for producing a therapeutic effect on a subject including rotating a configuration of one or more magnets adjacent the subject such that an electric field permeates the subject.

In one form, the therapeutic effect includes activating a nerve or muscle of the subject.

Hereafter the rotating magnet configuration is referred to as the rotor.

BRIEF DESCRIPTION OF THE DRAWINGS

A number of embodiments of the present invention will now be described, with reference to the accompanying drawings, wherein.

DETAILED DESCRIPTION INCLUDING BEST MODE

Figure 1:
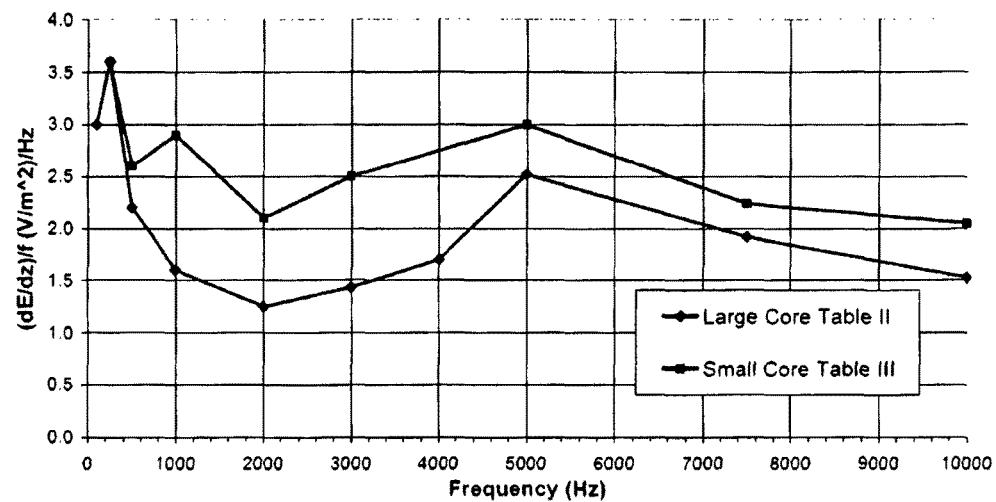
FIG. 1 is a graph analysing the experimental results in Tables II and III of Davey K., Luo L. & Ross D. A. "Toward Functional Magnetic Stimulation (FMS) Theory and Experiment", *IEEE Trans. on Biomedical Engineering*, Vol. 41, No. 11, November 1994, pp. 1024-1030, on the activation of sciatic nerves of African bullfrogs threaded through two different-sized toroidal cores, where the horizontal axis is the electric current frequency and the vertical axis is the ratio of the threshold electric field gradient divided by the frequency.

In the experiments by Davey et al. (ibid.), the sciatic nerves of African bullfrogs were threaded through two different-sized ferromagnetic toroidal cores carrying sinusoidal currents and the threshold electric field gradient for nerve activation was tabulated. To include the effect of duration of the electric field, it is instructive to examine the ratio of the threshold electric field gradient divided by the frequency. FIG. 1 shows that that ratio varied little from 100 Hz to 10,000 Hz, but had a minimum at 2,000 Hz where the threshold values were in the range 1 to 2 V/(m² Hz).

If tissue boundaries and other variations in resistivity are ignored, the electric field produced by a rotating magnet configuration can be evaluated from the negative time derivative of the magnetic vector potential determined using the Coulomb gauge, i.e. having zero divergence. For most permanent magnet materials, that magnetic vector potential can be evaluated by the Biot Savart Law based on the equivalent surface current around the permanent magnet. This is a good approximation for magnets such as the high magnetic remanence neodymium iron boron magnets which have relative differential permeability close to unity, i.e. close to that of air. The permanent magnet configurations disclosed below are particular configurations which have high gradient along a line of the component of the magnetic vector potential along that line, and further, that gradient reverses in sign when the configuration is rotated about some axis. As a result, during rotation, the negative time derivative of the magnetic vector potential gradient along the line, which equals the electric field gradient along the line, has a maximum (in its component along the line) at the instant when the magnetic vector potential gradient reverses.

For any rotating magnetic configuration, the amplitude of the electric field (and of its spatial gradient) increases proportional to the rotation frequency. The ratio of the electric field gradient divided by the frequency is therefore constant. The analysis provided in FIG. 1 of the experimental results of Davey et al. (ibid.) suggest that the diffusion behaviour of ions in the nerve fibre are such as to make frequencies around 2,000 Hz most favourable for stimulation, but that the threshold is not greatly higher for frequencies in the range 200 to 1,000 Hz, which are more easily achieved in rotating magnet configurations. For a magnet configuration which produces 1 cycle of magnetic flux density variation per rotation, 200 Hz corresponds to 12,000 rpm, while a configuration which produces 2 cycles per rotation generates 200 Hz at 6,000 rpm. Thus speeds of at least 5,000 rpm and more probably at least 10,000 rpm are likely to be needed.

Figure 2A:
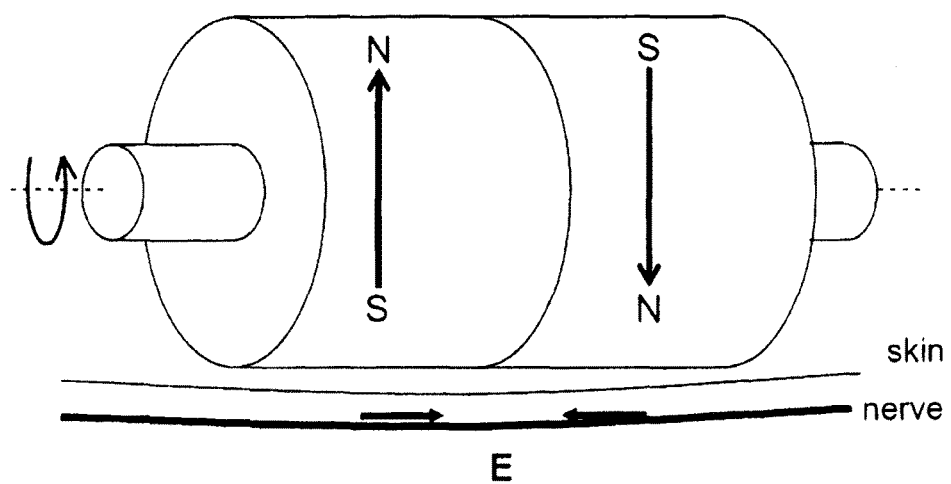
FIG. 2a is a sketch of the preferred embodiment of the invention being a two magnet "bipole" configuration designed primarily to activate a nerve fibre aligned parallel to the axis of the rotor, with the nerve fibre shown as running close to the surface of the tissue and parallel to the skin, magnetisation vectors shown as open-headed arrows and key electric field vectors shown as solid-headed arrows.

FIG. 2a shows the magnetic configuration of the preferred embodiment of the device, which comprises two adjacent cylindrical magnets, each diametrically magnetised in opposing directions (shown by the straight open-headed arrows). The circular arrow indicates the rotation axis of the configuration, which is parallel to the nerve fibre to be activated, shown in FIG. 2a as lying under and parallel to the skin. Not shown in FIG. 2a are the bearings supporting the rotor nor the stationary housing also supporting the bearings and optionally fixing the windings as described below. FIG. 2a depicts the rotor having a short shaft extending from each end, on which the inner race of roller bearings could be fixed, the outer race being fixed to the housing (not shown). The shaft could be stub shafts at each end of the magnet configuration or a single shaft could pass through holes in each magnet.

Figure 2B:
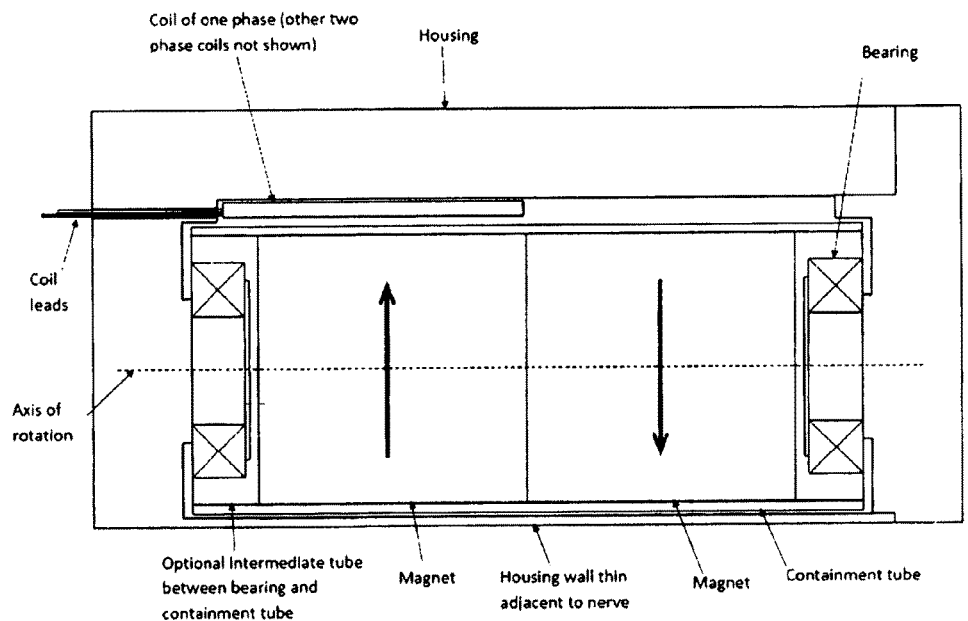
FIG. 2b depicts the cross-section of a possible bearing arrangement for the magnetic configuration of FIG. 2a, which is also applicable to some other magnetic configurations described hereafter.
Figure 7:
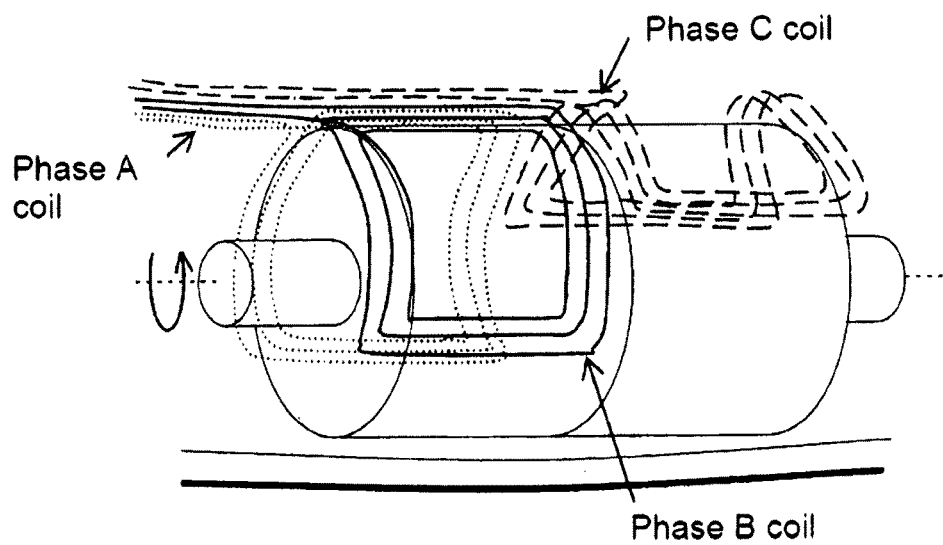
FIG. 7 depicts a winding configuration displaced about the environment of the rotor of FIG. 2 to produce its rotation.

FIG. 2b depicts a possible arrangement whereby the magnetic configuration of FIG. 2a can be mounted inside a housing. A cylindrical containment tube of some high strength material (such as Inconel or carbon fibre or the titanium-aluminium-vanadium alloy Ti-6Al-4V) is shown which may be applied over the magnet configuration to prevent the magnets flying apart during rotation because of their low tensile yield strength. Certain containment tubes can be applied by heat-shrinking. A possible bearing configuration is shown in which the containment tube is extended beyond each end of the magnet configuration and the outer race of each bearing is fixed to an annular ring internal to that tube, which is optionally integrally connected to a plate which seals the end of the magnet, protecting it from the environment. The inner race of each bearing is fixed to a stationary shaft extending axially inwards from the end of the housing. The intermediate annular ring provides an axial face from which a small amount of material could be drilled away to balance the rotor. Alternatively, the bearings could be sized to fit the internal diameter of the containment tube and the annular ring can be eliminated. The outer diameter of the magnets and the outer diameter of either the bearings or the intermediate annular tube (if present) can be made to precise diameters which can be very slightly different so that the containment tube applies different compression pressures on the magnets and on the bearings. This arrangement would not require holes through the magnets. The bearings should ideally be non-metallic to avoid eddy currents in the stationary race, and high-speed all-ceramic bearings are suitable. The housing of FIG. 2b is shown as being thinner on one side, that side to be placed against the tissue so that the magnets lie as close as possible to the nerve, and thicker on the other side in order to make the housing stiffer. One coil of a possible winding configuration to be described in FIG. 7 is shown. Screws or other fastening means for the housing end cap shown on the right of FIG. 2b have not been drawn.

The housing is non electrically conducting and non magnetic and can be made of a high quality engineering plastic such as acrylic or PEEK. This bearing and housing arrangement would be suitable for some of the other magnetic configurations described hereafter, but it is only one of many possible arrangements that could be used. Other possible arrangements of the housing and coils have uniform housing wall thickness. While the configuration shown in FIG. 2b may be slightly simpler to make than a more conventional configuration in which the rotor has shafts extending along the axis as in FIG. 2a, the latter conventional configuration has the advantage that the rotating race of the bearing is at smaller radius, which may enable slightly higher bearing rotation speed, due to lower mechanical stress in the bearing.

When rotating, each of the magnets in the configuration of FIG. 2a creates an electric field configuration with high peak values parallel to the axis of rotation outside the magnet at its mid-plane. Supposing that tissue boundaries and other variations in resistivity are ignored, then the electric field can be obtained from the negative time derivative of the magnetic vector potential determined using the gauge potential, i.e. having zero divergence. Peak electric field vectors are shown as solid-headed arrows in FIG. 2a. The electric field component at a point varies sinusoidally in time and has amplitude proportional to the rotation speed. The axial electric field gradient has a peak near the end-plane of the magnet. By juxtaposing two magnets with opposite directions, the electric field gradients from the two magnets sum at the mid-plane between them, thus doubling the electric field gradient that would have been present for just one magnet.

An analytical expression has been derived (Watterson, unpublished) for the peak electric field gradient of this configuration, ignoring tissue boundaries. The ratio of the electric field gradient to frequency is independent of frequency, as for any rotating magnet configuration, but drops off with distance from the magnet configuration. FIG. 3 plots that theoretical ratio for the bipole of FIG. 2, assuming high strength magnets of remanence 1.45 T, with each magnet cylinder having axial length the same as its diameter, though this is not a requirement but is rather a possible design dimensional ratio—shorter axial length is possible with only slightly diminished electric field gradient. Also shown as dashed horizontal lines on FIG. 3 are the threshold ratios measured on the sciatic nerves of African bullfrogs from Table II of Davey et al. (ibid.), being two points on the lower curve of FIG. 1, at particular frequencies, namely 500 Hz, which corresponds to 30,000 rpm, and 1,000 Hz, which corresponds to 60,000 rpm. The conclusion is that the observed threshold electric field gradients for nerve activation are reached for a nerve with separation up to 0.47 times the magnet radius from the magnet surface for 30,000 rpm and up to 0.63 times the magnet radius for 60,000 rpm. For a magnet of radius 15 mm, say, these separations are 7.0 mm and 9.5 mm, respectively. Allowing for a distance of say 2.5 mm between the magnet surface and the device housing perimeter, this means that nerves should be activated up to depths of 4.5 mm to 7 mm below the skin, for speeds between 30,000 rpm and 60,000 rpm. Proportionally larger magnets can be used for deeper nerves.

While the FIG. 1 presentation of the results from Davey et al. (ibid.) suggest that it would be advantageous for nerve activation to increase the rotation speed to 120,000 rpm or 2,000 Hz as this would correspond to the minimum in the threshold activation curve shown in FIG. 1, the mechanical stresses increase with speed and it will generally be preferable to accept a reduced speed below the optimum in order to increase the safety of the device against the risk of mechanical failure.

The above calculation has neglected the electric potential build up in the tissue outside the nerve, caused by blocking of circulating currents by the tissue boundary (in particular the skin) and other conductivity variations in the body. These effects will reduce the electric field, by an amount which must be calculated for the particular part of the body being exposed to the varying magnetic field. An example of the kind of calculation required to evaluate these effects, for the brain in this example, is given in Miranda P. C., Hallett M. & Basser P. J. "The Electric Field Induced in the Brain by Magnetic Stimulation: A 3-D Finite-Element Analysis of the Effect of Tissue Heterogeneity and Anisotropy" *IEEE Trans. On Biomedical Engineering*, Vol. 50, No. 9, 2003, pp. 1074-1085. Because of these effects, the nerve activation depths suggested by FIG. 3 would most likely be reduced when calculated for a particular body part.

Furthermore, the activation thresholds differ between nerve types and axon diameters and so the threshold values above based on bullfrog nerves should only be considered indicative for humans and will vary for the different nerves in a human.

Figure 2C:
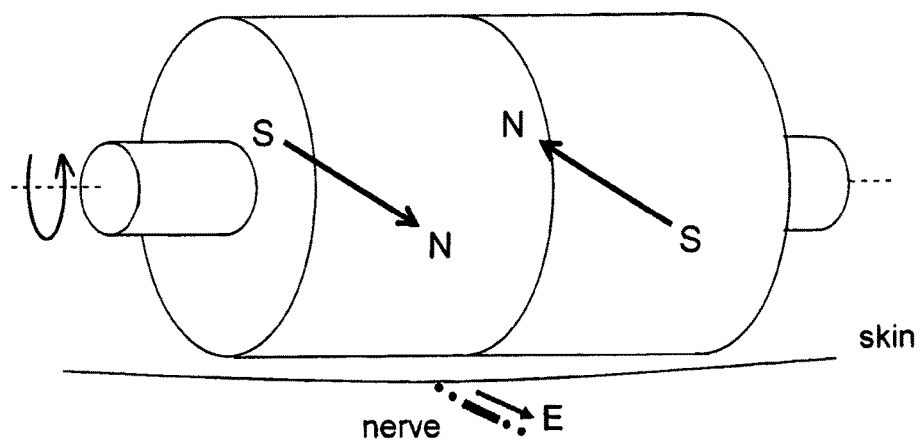
FIG. 2c is a sketch of the preferred embodiment of the invention when used to activate a nerve perpendicular to the axis of the rotor, shown at the instant when the magnetisation direction vectors shown as open-headed arrows are horizontal and the perpendicular electric field shown as a solid-headed arrow immediately under the middle of the rotor is at its peak.
Figure 3:
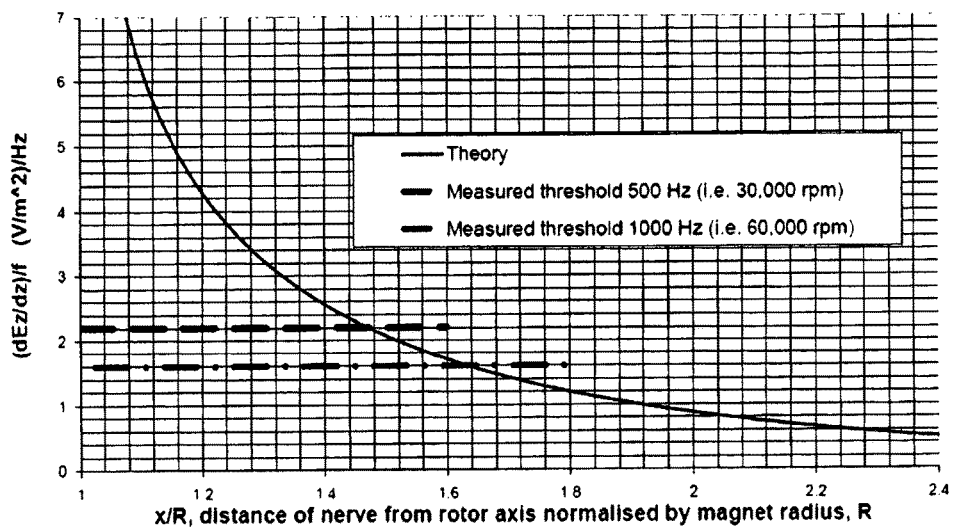
FIG. 3 is a graph showing the dependence on distance from the rotor axis for the preferred embodiment of the peak parallel electric field gradient divided by the frequency, indicating where that ratio exceeds the threshold values reported in Table II of Davey et al. (ibid.) for 500 Hz and 1,000 Hz.

The magnetic configuration of FIG. 2 also creates an electric field component along a nerve fibre perpendicular to the axis of rotation, which has peak value on the intersection of the plane between the magnets immediately under the magnets when they are horizontal as depicted in FIG. 2c. Since the electric field falls away with distance from the plane perpendicular to the skin and containing the rotor axis, there is a peak in the electric field gradient at some distance on either side of that plane. This peak could also be used to activate nerves. The peak of the perpendicular electric field itself is double in amplitude because of the presence of the two magnets. The high peak amplitude may be useful in stimulating curved nerves.

Figure 4:
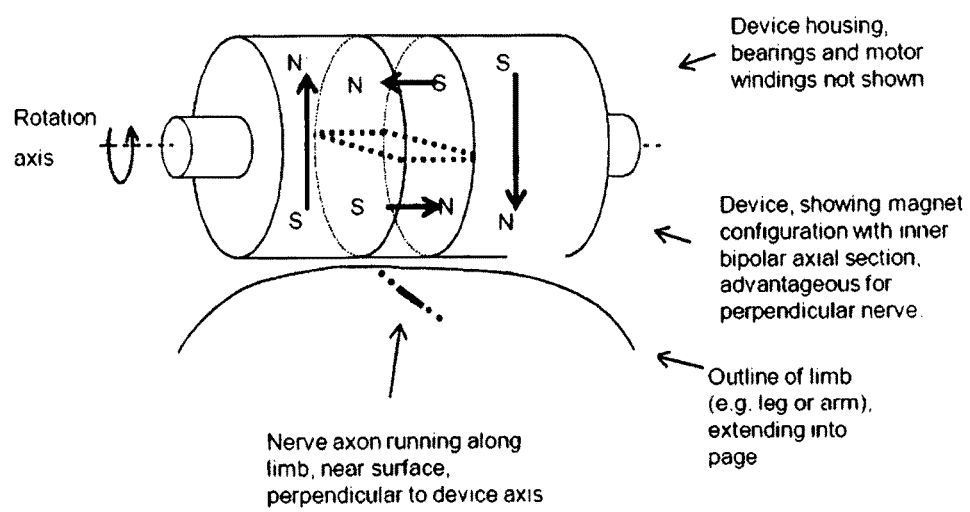
FIG. 4 is a sketch of a second embodiment of the invention designed to more effectively activate a nerve fibre aligned perpendicular to the axis of the rotor, with the axis of the rotor parallel to the skin.

FIG. 4 shows a second embodiment of the invention which is a variation of the magnetic configuration of FIG. 2 designed to increase the peak in the perpendicular electric field gradient at an offset distance from the plane through the rotor axis, as described in the previous paragraph. The variation is to add two magnet half-cylinders, magnetised axially in opposite directions, placed in between the diametrically magnetised cylinders. At the instant shown in FIG. 4, the magnetic vector potential component along the nerve fibre, into the page, is at a maximum and so the electric field component along the nerve is zero at the instant shown, but a quarter of a rotation period later it would be maximal along the nerve immediately under the magnets, i.e. on the plane including the axis of the rotor and perpendicular to the nerve fibre. This configuration thus has enhanced peak electric field and also enhanced electric field gradient, from the spatial decay in amplitude away from that peak.

Figure 5A:
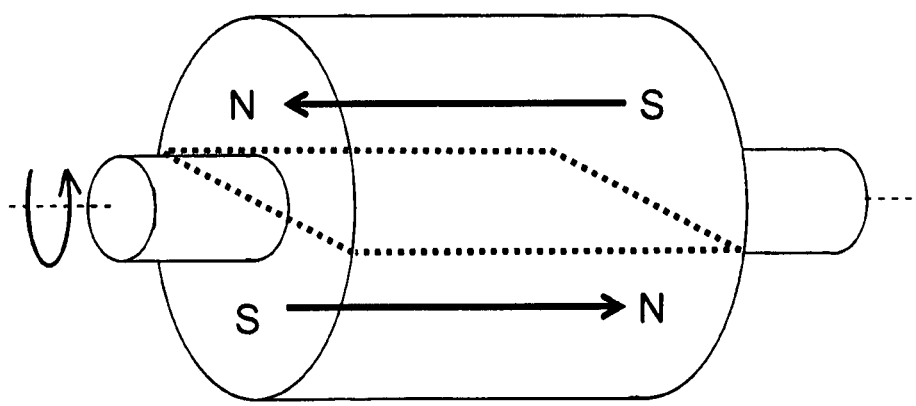
FIG. 5a is a sketch of a third embodiment of the invention, comprising two axially magnetised half cylinder magnets with magnetisation direction vectors shown as open-headed arrows.
Figure 5B:
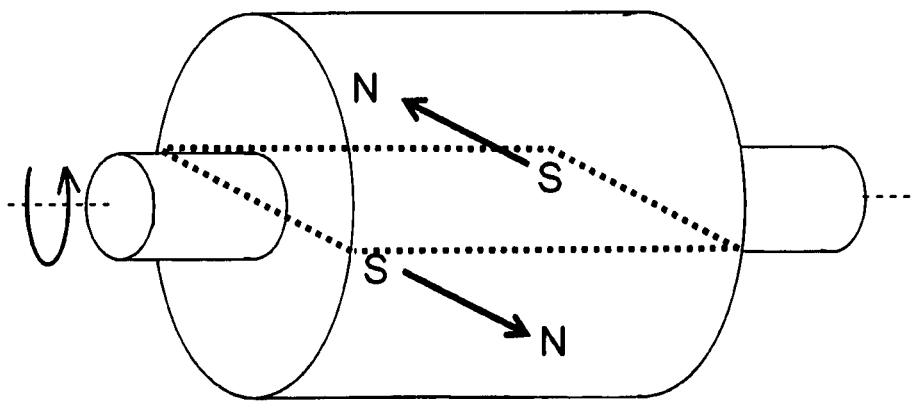
FIG. 5b is a sketch of a fourth embodiment of the invention, comprising two diametrically magnetised half cylinder magnets with magnetisation direction vectors shown as open-headed arrows.

A configuration consisting of the two axially magnetised half cylinders alone could also be used, its preferred application being with axis parallel to the skin to stimulate a nerve perpendicular to the axis by creating a peak in the perpendicular electric field under the middle of the device, with associated gradients in the electric field from its decay in amplitude away from that peak. The rotor is depicted in FIG. 5a and resembles that shown in FIG. 4 but without the end diametrically magnetised magnets and with the axially magnetised magnets optionally of longer axial length. The axis of the rotor could also be positioned perpendicular to the skin in which case it would generate a peak electric field tangential to the skin at a point on the axis. The two magnet half cylinders could also be magnetised diametrically, in opposite directions parallel to their planar cut surfaces as depicted in FIG. 5b. The preferred application of this configuration is with axis parallel to the skin to activate a nerve parallel to the rotor axis by creating a peak in the axial electric field under the middle of the device, with associated gradients in the electric field associated with its decay in amplitude away from that peak. Alternatively, with axis perpendicular to the skin it would create oscillating antiparallel converging electric fields along any nerve line parallel to the tissue surface and passing under the axis of the device with peak electric field gradient on the axis of the device. In either of these uses of the configuration of FIG. 5b, the dominant frequency of the variation would be double the rotation frequency, and the quicker time variation would increase the electric field amplitude and may bring the frequency closer to a preferred nerve or muscle stimulation frequency. The two configurations of FIG. 5 described in this paragraph plus the bipole configuration of FIG. 2a together constitute the three ways in which a cylindrical body can be cut from two magnets with opposite magnetisation directions joined on a plane.

A variation on the magnet configurations of FIG. 2 and FIG. 4 that would enable nerve activation at multiple locations is to extend the rotors axially by repeating the magnet pattern with alternating magnet directions. For the configuration of FIG. 2, additional magnet cylinders, diametrically magnetised, can be added with alternating magnetisation direction. The electric field gradient along a nerve running parallel to the axis would have peaks at each plane of contact between magnet pairs, and peaks of the required sign for activation on opposite sides of the rotor. For the configuration of FIG. 4, however, different nerves perpendicular to the rotor axis could be activated by the rotor if it is extended axially, repeating the pattern of diametrically magnetised magnets and intermediate axially aligned half-cylinder magnets. The half-cylinder magnets could be omitted but they increase the electric field gradient amplitude for perpendicular nerves.

Figure 6:
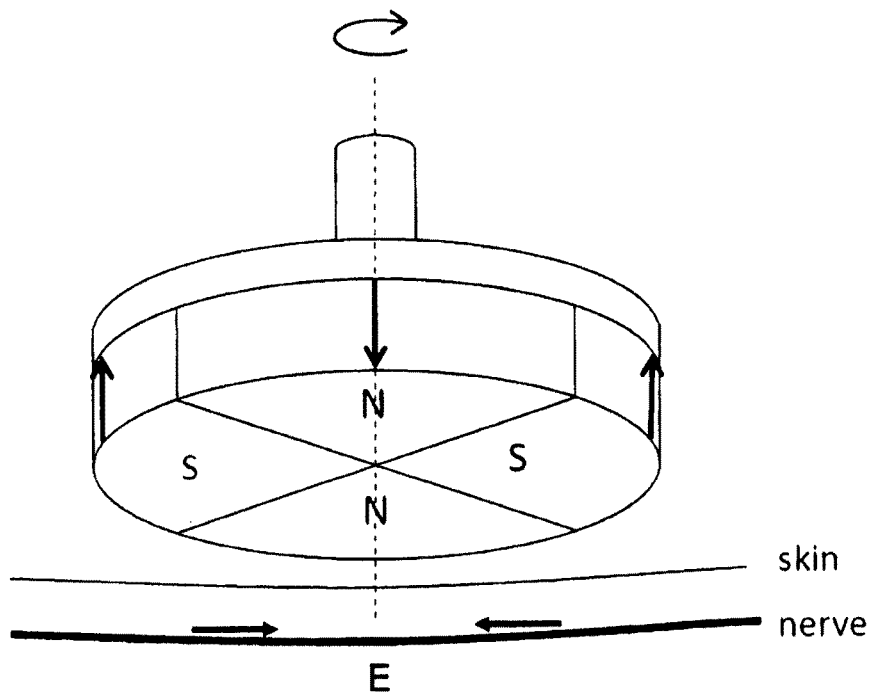
FIG. 6 is a sketch of a fifth embodiment of the invention, comprising a "quadrupole" configuration with the axis of the rotor perpendicular to the skin and to the nerve fibre, magnetisation vectors shown as open-headed arrows and key electric field vectors shown as solid-headed arrows.

FIG. 6 shows the magnetic configuration of a fifth embodiment of the invention, comprising an arrangement of four right-angle sector magnets, axially magnetised and placed, with alternating polarity on a ferromagnetic backing plate, which could be made of a ferromagnetic steel such as mild steel or a magnetic grade of stainless steel. The magnets need not be complete right-angles, they could be circular for example, but the electric fields induced are strongest for complete sectors. The ferromagnetic plate has several significant advantages, namely: it stops leakage of the magnetic flux into the region behind the plate, away from the tissue; it increases the magnetic flux density inside the tissue where the nerve lies; and it provides a means of support for the magnets. For deeper magnets the ferromagnetic plate need not be used. A more complicated "Halbach array" of more magnet sectors could be used but still creating a quadrupole field emerging from the device bottom plane. To avoid a bearing race lying between the rotor and the nerve, both bearings could be positioned on the shaft above the magnet configuration. A containment tube should surround the magnetic configuration as otherwise the magnets might crack and fly outwards given their weak tensile strength.

For a nerve that passes through the centre line of this magnetic configuration, the electric fields from either side of the rotor are equal and opposite at a time when the middle of two magnet quadrants lie above the nerve. The electric field vectors are drawn as solid-headed arrows in FIG. 6. This creates a peak in the electric field gradient at the point on the centre-line, which is double what it would be for just one of those two magnet quadrants acting alone. The frequency of the electric field oscillation is also double the rotation frequency, which enables it to be nearer the optimum 2,000 Hz frequency realised in FIG. 1 at a lower rotation speed, or 2,000 Hz itself at 60,000 rpm.

Another advantageous feature of this quadrupole configuration if it has no ferromagnetic backing plate is that the electric field derived from the rotating magnetic field alone, ignoring tissue boundaries and resistivity in homogeneities, lies only in planes perpendicular to the axis of rotation. For a broad region of tissue with skin surface close to planar in the vicinity of the device, the skin surface would not block currents generated by this device, because the currents lie in parallel planes to the skin. Thus the reduction in the electric field due to the primarily planar local tissue boundary is less for this configuration. The same advantage applies for any configuration of magnets which are all magnetised parallel to the direction of the rotation axis of the configuration, when the rotation axis is positioned perpendicular to the skin. The presence of ferromagnetic backing may reintroduce some perpendicular electrical potential gradients on the surface.

Another magnetic configuration related to that of FIG. 6 which also has like polarity magnets on either side of the axis, providing a doubling of the electric field gradient on the axis, is one with eight axially aligned magnet sectors. This is another possible configuration for activation, but it would suffer from a reduced penetration depth of the magnetic field into the tissue compared to the quadrupole configuration of FIG. 6.

It is possible to spin each of the above magnetic configurations by a separate rotary motor axially displaced from the magnetic configuration. However this may have several drawbacks. Firstly, the device would be longer axially than the magnet configuration alone. Secondly, for the configurations of FIG. 2 and FIG. 4 which are elongated axially, both the motor and the magnet configuration would need their own pair of bearings and there would need to be a coupling in between the shafts of the rotors, which would produce some mechanical loss and be prone to failure. Thirdly, again for these configurations and others with no iron used in the magnet configuration, if there were a motor in the vicinity including ferromagnetic parts then those parts may draw magnetic flux from the magnet configuration, perturbing the configuration magnetic field and also producing eddy current losses in any stationary metallic parts of the motor.

An alternative disclosed herein is for the magnets of the magnet configuration for nerve activation to be driven to rotate by their own interaction with alternating currents in coils suitably positioned around the magnet configuration. Those currents produce a magnetic field (by Ampere's Law) that interacts with the magnetic field of the magnetic configuration to effect its rotation. There are many possible coil arrangements of varying complexities and efficiencies that could be used, a few of which are described below.

The torque required to spin the rotor is small because the only external load torque is that associated with the small eddy losses generated in the tissue due to its small conductivity. The other loss torques are those due to windage on the rotor, bearing losses, and eddy losses in the winding themselves. The latter may be minimised by using finely-stranded "Litz" wire. Metallic or other electrically conducting material should not lie close to the device as eddy currents may be generated in the conducting material. The total loss is typically in the range 1 Watts to 30 Watts and is sufficiently low that the device can be powered by a small battery, making the device easily portable. This is much lower power than pulsed coil devices, for example the MagPro X100 made by MagVenture A/S of Denmark requires peak power 2,300 Watts ("MagPro X100 With Option, Technical Data", MagVenture A/S, October 2007).

FIG. 7 sketches one possible coil configuration suitable for the magnetic configuration of the preferred and second embodiments. There are three coils to be fed by three-phase alternating current, with the currents in the phases displaced by 120 electrical degrees from each other. The coils need not be very thick since the torque required to spin the rotor is very small. However, ideally the coils should not lie in the gap between the magnet surface and the nerve fibre, thereby increasing their separation. The coil configuration disclosed in FIG. 7 is one such configuration with all coils kept away from the strip above the nerve fibre. Each coil is identical and spans an azimuthal arc of approximately 120 degrees to its perimeter. Two coils act on one of the magnets and the third coil acts on the other magnet. Three turns are depicted in each coil of FIG. 7 but this is schematic—the coils could have more or fewer turns, the number chosen to suit the desired inverter voltage at the maximum speed. Coils of two layers could be used to avoid the lead-in conductor having to cross the other turns.

The above magnet configuration and coils form an "ironless" brushless permanent magnet motor. In conventional motors, a laminated silicon steel "yoke" keeps the magnetic flux inside the motor. This motor has no such containing steel and the magnetic field penetrates both the windings configured in the case around the rotor and into the tissue where the nerve is located. It would be possible to place a laminated or soft-magnetic-composite arc over the side of the rotor away from the nerve. However, as well as introducing high "iron losses", there would be a high force of attraction between the iron and magnet which would wear the bearings and induce bearing loss, and there would also be oscillating "cogging torque" between the magnets and iron.

For the fifth embodiment, three planar triangular coils could be placed in the housing between the skin and the quadrupole configuration. As this would increase the nerve to magnet separation slightly, an alternative would be to position three or six coils radially outside the magnet configuration, in order to pick up the magnetic flux passing from each magnet quadrant out and back to the ferromagnetic backing disk. This magnetic flux density is much weaker however, and so either the copper ohmic losses would be higher for that coil positioning or thicker coils could be used.

Similarly for the first and second embodiments, magnetic flux at the ends of the rotor between the magnet poles could be collected in coils placed axially beyond the rotor. However the space there is limited by the bearings and the flux densities are again weaker there.

A three-phase inverter can drive the currents in the coils. The inverter should be placed at sufficient distance from the device to avoid eddy currents. Ideally, the inverter used should be of sensorless switching type in order to avoid having to add sensors to detect the rotor angle. Inductors may be added for each phase at the inverter to obviate the problem of the winding having very low inductance, which otherwise implies high current ripple at the switching frequency.

There are many other possible topologies for the coils obvious to those skilled in the art of motor design. The coils depicted here are all "short-pitched" which is advantageous as they are non-overlapping. A class of alternative coil configurations are those which use "full-pitched" coils, linking the maximum possible magnetic flux, but these would entail overlapping end-windings which would increase the winding's radial thickness. Another class of alternative topologies are those with only two coils spaced 90 degrees apart to create two-phase windings.

Although magnetic configurations with several magnets combining to increase the electrical field gradient at a point have been described above, the combination of a rotating, single magnet and ironless coil configuration surrounding it may also provide nerve activation.

Figure 8:
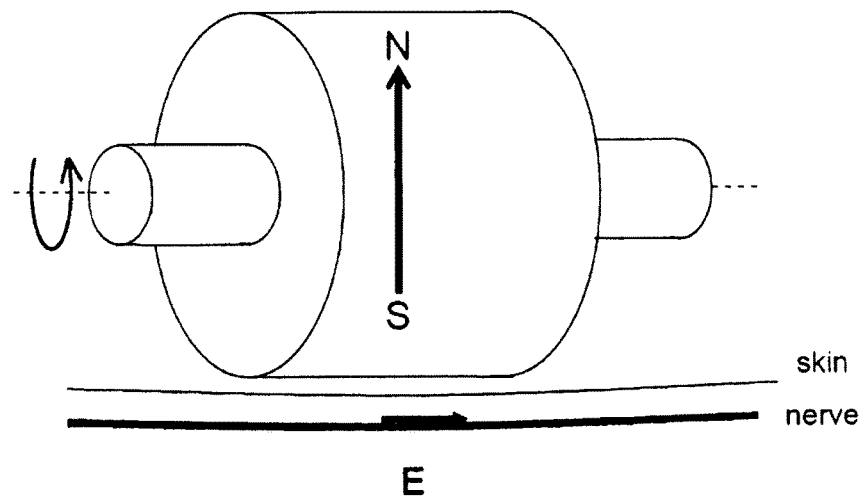
FIG. 8 depicts a sixth embodiment of the invention with a single magnet configuration with axis parallel to the nerve, magnetisation vector shown as an open-headed arrow and electric field vector shown as a solid-headed arrow.

FIG. 8 shows the magnetic configuration of a sixth embodiment of the invention. In this embodiment, a single cylindrical magnet diametrically magnetised is rotated about an axis. The preferred use of this configuration is to orient the axis parallel to a nerve lying under the skin as shown in FIG. 8. The electrical field has a peak under the magnet as shown and the electric field gradient has a peak in the vicinity of each magnet end-plane. Although the electric field gradient is half that of the embodiment shown in FIG. 2 at its mid-plane, there is some constructional simplification in only having one magnet. This would enable an increased speed, bringing the electric field frequency closer to the nerve's most favourable activation frequency which may compensate for the electric field drop. The nerve could also be aligned perpendicular to the rotor axis and in the magnet end-plane, in which case the electric field gradient would be slightly less than half that of the second embodiment in FIG. 4. There are many possible ironless winding configurations suitable for this spinning single magnet. One winding which does not impinge on the gap between the nerve and magnet is that of FIG. 7 but with the coil which is on its own in FIG. 7 shifted axially to overlap the other two coils. Another winding is shown in FIG. 9.

Figure 9:
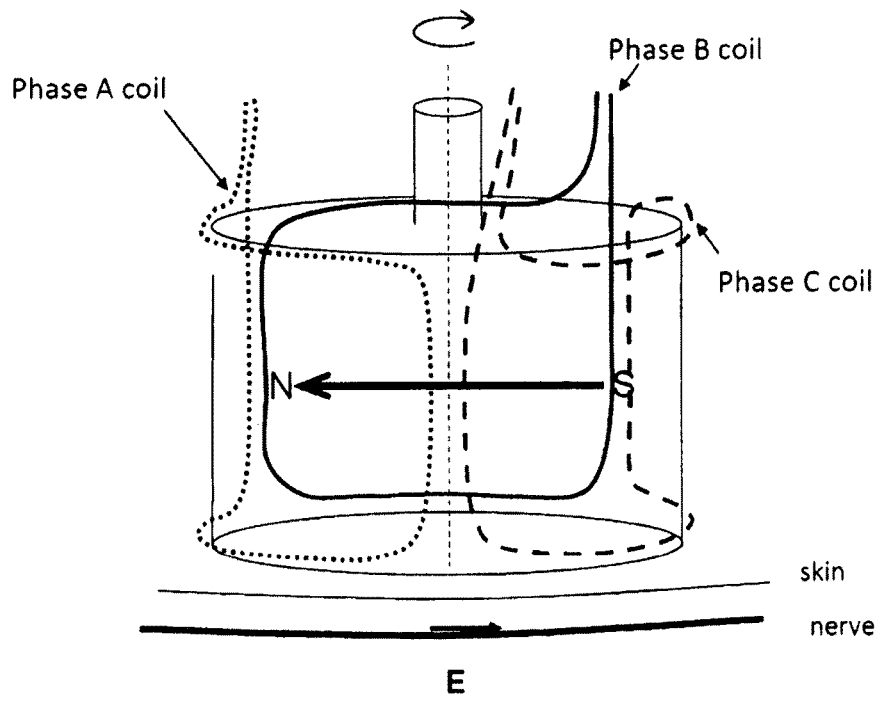
FIG. 9 depicts a seventh embodiment of the invention, with a single magnet configuration with axis perpendicular to the nerve, showing a possible three-phase coil configuration, magnetisation vector shown as an open-headed arrow and electric field vector shown as a solid-headed arrow.

FIG. 9 shows the magnetic configuration of a seventh embodiment of the invention. In this embodiment a single cylindrical magnet diametrically magnetised is rotated around an axis perpendicular to the skin. The electric field component along the nerve has a peak on the axis and the gradient has peaks at two points along the nerve in each direction. A possible three-phase winding is shown positioned around the magnet. Only one turn of each coil is shown but many turns may be used, as described above in relation to FIG. 7.

Figure 10:
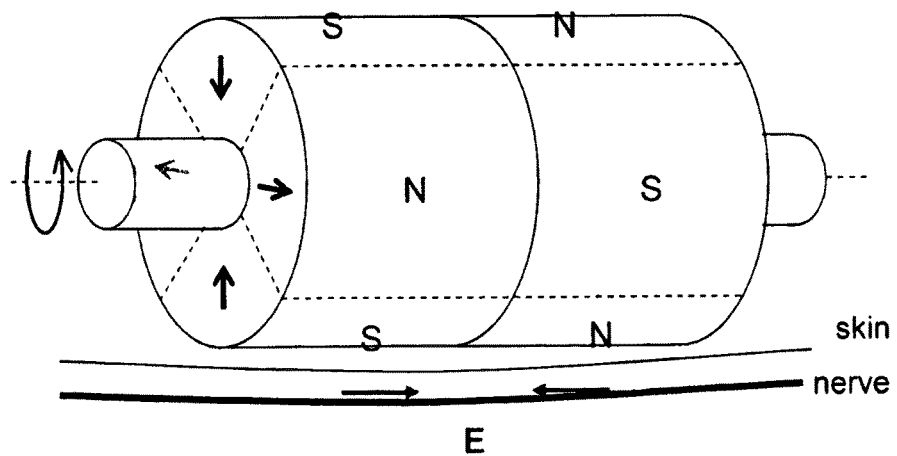
FIG. 10 depicts an eighth embodiment of the invention, comprising a configuration of eight magnetic poles, with four alternating poles displaced around each end of an axis of rotation and with the poles being of opposite polarity at the two axial ends, one possible arrangement of magnetisation vectors shown as open-headed arrows and electric field vectors shown as solid-headed arrows.

FIG. 10 depicts the magnetic configuration of an eighth embodiment of the invention. This embodiment is similar in type to that of FIG. 2 but at each axial end of the configuration there are four alternating magnetic poles instead of two. The magnetic poles at any angle with respect to the axis are opposite at the two ends of the rotor, which creates the converging electric field vectors as shown in FIG. 10 in the same way as described for FIG. 2a. The four magnetic poles at each end could be created by various arrangements of magnets. One arrangement as suggested in FIG. 10 would be to join four magnets each shaped as a quadrant of a cylinder and with their magnetisation directions rotated by 90 degrees between each magnet. The magnets could be mounted on a ferromagnetic cylindrical shaft. Another arrangement to create the four magnetic poles at an end would be that shown in FIG. 5b comprising just two magnets diametrically magnetised since that arrangement also creates four magnetic poles, each spanning 90 degree around the axis though with higher flux densities near the poles where they lie on either side of the cut plane of the magnets. Yet another arrangement would be to create the four pole configuration from a "Halbach" array of wedge-shaped magnets. This eighth embodiment of the invention could be used with axis parallel to the skin and could either stimulate a nerve parallel to the axis via the high electric field gradient formed from the convergence of axial electric fields at the mid-plane of the device, as drawn in FIG. 10, or it could stimulate a nerve perpendicular to the axis and lying in the mid-plane of the device via the electric field gradient associated with the decay in the electric field moving away from a peak in the perpendicular electric field immediately under the device. This embodiment would have the advantage that the nerve would experience a double frequency excitation, which may bring it closer to a higher optimum excitation frequency, for example the 2,000 Hz suggested by FIG. 1. A disadvantage of this configuration compared to the preferred embodiment is that the penetration depth of the electric field into an adjacent body would be lower.

Figure 11:
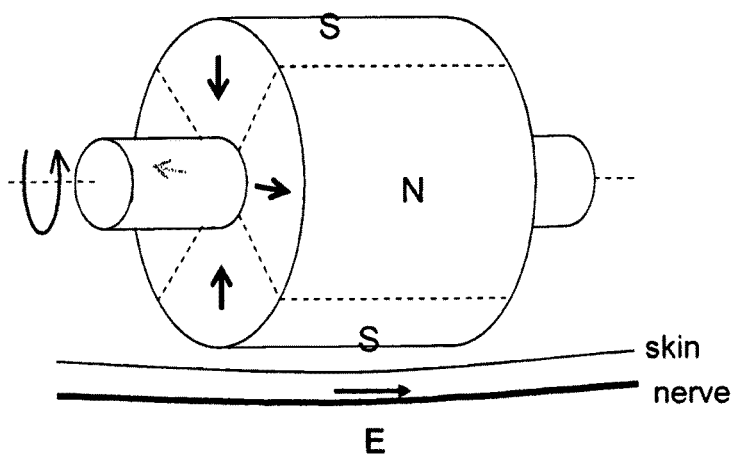
FIG. 11 depicts a ninth embodiment of the invention, comprising a configuration of four alternating magnetic poles displaced around the axis of rotation, one possible arrangement of magnetisation vectors shown as open-headed arrows and an electric field vector shown as a solid-headed arrow.

FIG. 11 depicts the magnetic configuration of a ninth embodiment of the invention, in which there are four magnetic poles of alternating polarity around the axis of rotation of the rotatable configuration (in one example each pole forms a quadrant of a cylinder however it will be appreciated that each pole need not necessarily span 90 degrees with respect to the direct of rotation). This embodiment is related to the eighth embodiment of FIG. 10 being the simplification of only including one axial end of that configuration. The configuration of FIG. 5b can also be considered of this type as it has four magnetic poles around the axis, though with higher flux densities near the poles where they lie on either side of the cut plane of the magnets. This ninth embodiment could stimulate a nerve lying either parallel to the axis or perpendicular to the axis and near the end-plane of the device. This embodiment would have half the peak electric field gradient of the eighth embodiment but it would have the advantage of being shorter and easier to make.

There are many other possible magnet configurations capable of producing high electric field gradients along a line when rotated, and only some of the more effective and easily constructed configurations have been described above. Rotors with cylindrical perimeters have been shown in the figures because these are more simply constructed with the precise dimensions needed for heat-shrinking of a containment tube. However other perimeter shapes could be used. Only magnet configurations which are axisymmetric and are rotated around their symmetry axis produce no electric field gradients whatsoever.

While the intended purpose of the devices disclosed herein is for activation of nerve cells, there are several possible alternative therapeutic applications. When the devices disclosed herein are operated at frequencies and acting on nerves at distances such that the electric field gradient is below the threshold for nerve activation for the frequency, the devices may instead block the passage of an action potential along the nerve. As such the device could be used to block pain signals, which could be of great benefit to sufferers from many ailments, such as a bad back and peripheral neuropathy. Magnetic configurations which create multiple triggering sites with peak electric field gradients occurring at staggered times may be superior in that application. Another possible application is hyperthermia; for larger magnetic configurations spun to very high speed there could be sufficient eddy currents in the tissue to heat it. Other possible beneficial effects might include increased blood flow, wound healing, nerve regeneration, sexual stimulation and muscle conditioning. The devices may also directly activate muscle fibres causing muscle contraction without intermediate nerve stimulation. The devices may also be used to obtain diagnostic information about the nerves or muscles of a subject.

A further possible medical application of the devices disclosed herein is for transcutaneous energy transmission systems (TETS). Appropriately shaped coils implanted in the body could receive the electric fields generated in the body by the devices positioned outside the body, and thereby extract electrical power for use by an implanted device such as an artificial heart.

Outside of medical applications, the devices disclosed herein may be applied for other purposes requiring the penetration of electric fields or electric field gradients into a volume or on the surface of a volume.

EXAMPLE 1

Figure 12:
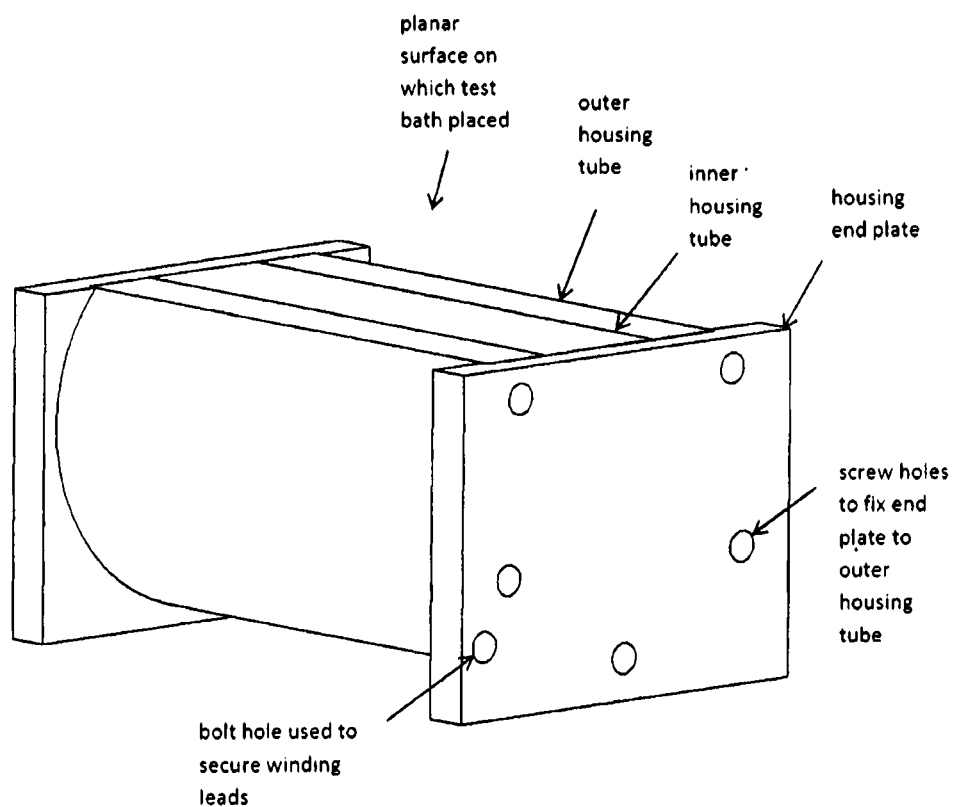
FIG. 12 is a drawing of one example of a housing of a device according to one example of the invention.

A device in accordance with the preferred embodiment of the concept, the bipole configuration of FIG. 2a, was constructed. FIG. 12 shows the housing of the device. Magnets of sintered neodymium iron boron with magnetic remanence of 1.45 T were used, each with diameter and axial length both 30 mm. A containment tube of Ti-6Al-4V was heat shrunk onto the magnets. This device used stub shafts at each end of the rotor, with all ceramic bearings made of zirconia oxide. The winding was of the type disclosed in FIG. 7, with 3 turns per coil, made of copper Litz wire. The coils were positioned in pockets on the outer surface of an inner housing tube made of ABSPlus by 3D printing. That tube was inserted into a thicker outer housing tube made of polycarbonate, which was screwed to polycarbonate housing end plates which included the outer bearing seats. The housing was cut to a planar surface on one side, offset 18 mm from the axis. A small commercial sensorless brushless DC motor electronic speed controller from the radio-controlled toy market was used to drive the motor. The controller's starting algorithm requires modification to suit the rotor inertia, and an initial mechanical twist was needed on the shaft. Inductors of 52 microH per phase were added to smooth the phase ripple current. The device has been tested up to 60,900 rpm corresponding to 1,015 Hz, but was generally run up to 930 Hz requiring 9.24 V DC supply. The required total input power was approximately $3 \times 10^{-5}$ W/Hz$^2$, for example 7.5 W at 500 Hz, primarily from windage loss and bearing loss, the latter possibly being higher due to additional bearing load associated with rotor imbalance.

A first series of physiological tests have been conducted applying the device to the sciatic nerve and gastrocnemius muscle of 6 Cane Toads (*Bufo Marinus*), following a protocol approved by the Animal Care and Ethics Committee of the University of Technology, Sydney. The nerve, of typical length 60 mm, and attached muscle, of typical length 30 mm, were placed in a rectangular Perspex bath of inner dimensions 85×85×35 mm, floor thickness 0.6 mm, filled to depth 10 to 20 mm with Toad Ringer's Solution. Usually the nerve was positioned as low as possible by adjusting threads tied around the nerve cut end and around the Achilles' heel at the muscle end. Stimulation was indicated by muscle contraction. Usually, double-sided tape held the bath on top of the device planar surface, though in one test the bath was elevated just off the surface by thread, and stimulation was still witnessed, precluding vibration as the cause.

Results varied considerably between toads, with the time from the nerve-muscle dissection, and with the height of the nerve. Some observations were as follows.

Firstly, some muscle contractions seen were apparently due to direct muscle stimulation, most readily for a muscle at the device centre aligned parallel to the axis, at frequency as low as 180 Hz (rounded to the nearest 10 Hz). The stimulation occurred with the sciatic nerve elevated away from the device. Small intramuscular nerves may have been stimulated but in one test Tubocurarine was administered to block the passage of neurotransmitter between the nerves and muscle and the contractions still occurred.

Secondly, stimulation of a straight nerve was confirmed in one nerve-muscle, at frequency as low as 240 Hz when the nerve was perpendicular to the axis, and as low as 770 Hz when the nerve was parallel to the axis. The muscle was placed vertically distant by 8 mm from the device and the site of the stimulation was confirmed as the sciatic nerve by the contraction of the muscle not occurring when the nerve was moved away from the device and placed in the vicinity of the muscle. In 1 other of the 6 nerve-muscles tested with a straight parallel nerve, contractions were seen but those contractions were probably due to muscle stimulation, rather than nerve stimulation, because contractions did not occur in other tests on that nerve-muscle with the muscle more distant. In 1 other of the 4 nerve-muscles tested for a straight low perpendicular nerve the muscle contracted when its tip was 18 mm horizontally from the axis, probably too radially distant to be stimulated directly, suggesting, nerve stimulation for that nerve-muscle also, hence for 2 of the 4 nerve-muscles tested with a low perpendicular nerve.

Thirdly, stimulation of nerves wrapped one half turn around a pillar of diameter 2.9 mm was seen and occurred most readily for the pillar on the centre with the nerve perpendicular, at frequency as low as 230 Hz.

The foregoing describes the principles of the present invention, and modifications, obvious to those skilled in the art, can be made thereto without departing from the scope of the invention. In the context of this specification, the word "comprising" means "including principally but not necessarily solely" or "having" or "including", and not "consisting only of". Variations of the word "comprising", such as "comprise" and "comprises" have correspondingly varied meanings.

The claims defining the invention are as follows:

1. A device including a rotatable configuration of magnets wherein rotation of the configuration of magnets about an axis of rotation produces an electric field in a volume around or adjacent to the device, and
    wherein the rotatable configuration of the magnets includes a first magnet and a second magnet wherein the first magnet and the second magnet are cylindrical and diametrically magnetized, the magnetization directions of the first magnet and the second magnet being aligned anti-parallel, and
    wherein an axis of revolution of the cylindrical first magnet and an axis of revolution of the cylindrical second magnet are coaxial, and
    wherein the axis of rotation of the rotatable configuration is coaxial with the axis of revolution of the cylindrical first magnet and the axis of revolution of the cylindrical second magnet, and
    wherein the device includes three coils each spanning approximately 120 degrees about the axis of rotation of the rotatable configuration, two of the coils positioned at one end of the rotatable configuration with respect to the axis of rotation of the rotatable configuration and the third coil positioned at the other end with respect to the axis of rotation of the rotatable configuration, wherein the three coils are arranged substantially on a first side of the rotatable configuration with respect to the axis of rotation, and
    wherein each of the three coils is arranged to receive a current and to thereby produce a related magnetic field, the magnetic fields of the three coils cooperating to interact with the magnetic field of the rotatable configuration of magnets to rotate the configuration of magnets.

2. A device according to claim 1, wherein the first magnet is positioned adjacent to the second magnet.

3. A device according to claim 1 wherein the rotatable configuration of magnets includes:
    a magnetic disc formed of two substantially semicircular halves, the halves being axially magnetised in opposite directions,
    wherein the disc is positioned between the first magnet and the second magnet.

4. A device according to claim 1, wherein the device generates an electric field capable of activating a nerve and/or muscle.

5. A device according to claim 1, wherein the configuration of magnets rotates at a speed exceeding 10,000 revolutions/minute.

6. A method of using a device according to claim 1 on a subject, including rotating the configuration of magnets of the device adjacent to the subject such that an electric field permeates the subject, to produce any one or a combination of therapeutic effects on the subject, said therapeutic effects selected from treating pain, generating localised hyperthermia, aiding in wound healing, providing nerve regeneration, providing muscle conditioning, increasing blood flow, and heating tissue, and/or to provide sexual stimulation.

7. A method of obtaining diagnostic information about the nerves or muscles of a subject, the method including locating the device according to claim 1, in a position wherein the electric field produced by rotation of the configuration of magnets of the device activates either the nerves or the muscles of the subject.

8. A device including a rotatable configuration of magnets wherein rotation of the configuration of magnets about an axis of rotation produces an electric field in a volume around or adjacent to the device, and
    wherein the rotatable configuration of the magnets includes a first magnet and a second magnet wherein the first magnet and the second magnet are cylindrical and diametrically magnetized, the magnetization directions of the first magnet and the second magnet being aligned anti-parallel, and
    wherein an axis of revolution of the cylindrical first magnet and an axis of revolution of the cylindrical second magnet are coaxial, and
    wherein the axis of rotation of the rotatable configuration is coaxial with the axis of revolution of the cylindrical first magnet and the axis of revolution of the cylindrical second magnet, and
    wherein the configuration of magnets is encased within a containment tube, and comprises supporting bearings located internal to the containment tube, wherein an outer race of the bearings is fixed to rotate with the containment tube, and an inner race of the bearings is fixed to a stationary shaft extending axially inwards from the containment tube.

9. A method for producing a therapeutic effect on a subject including rotating a configuration of magnets about an axis of rotation adjacent the subject such that an electric field permeates the subject,
    wherein the configuration of magnets includes a first magnet and a second magnet, and wherein the first magnet and the second magnet are cylindrical and diametrically magnetised, and the magnetisation directions of the first magnet and the second magnet are aligned anti-parallel, and
    wherein an axis of revolution of the cylindrical first magnet and an axis of revolution of the cylindrical second magnet are coaxial, and
    wherein the axis of rotation of the configuration of magnets is coaxial with the axis of revolution of the cylindrical first magnet and the axis of revolution of the cylindrical second magnet, and
    wherein included within the space surrounding the rotatable configuration of magnets are three coils each spanning approximately 120 degrees about the axis of rotation of the rotatable configuration, two of the coils positioned at one end of the rotatable configuration with respect to the axis of rotation of the rotatable configuration and the third coil positioned at the other end with respect to the axis of rotation of the rotatable configuration, wherein the three coils are arranged substantially on a first side of the rotatable configuration with respect to the axis of rotation, and wherein each of the three coils is arranged to receive a current and to thereby produce a related magnetic field, the magnetic fields of the three coils cooperating to interact with the magnetic field of the rotatable configuration of magnets to rotate the configuration of magnets.

* * * * *